United States Patent [19]

Mikkelsen et al.

[11] Patent Number: 5,312,527
[45] Date of Patent: May 17, 1994

[54] VOLTAMMETRIC SEQUENCE-SELECTIVE SENSOR FOR TARGET POLYNUCLEOTIDE SEQUENCES

[75] Inventors: Susan R. Mikkelsen, Montreal; Kelly M. Millan, LaSalle; Aleksandrs J. Spurmanis, Montreal, all of Canada

[73] Assignee: Concordia University, Canada

[21] Appl. No.: 957,602

[22] Filed: Oct. 6, 1992

[51] Int. Cl.$^5$ .............................................. G01N 27/26
[52] U.S. Cl. ................... 204/153.12; 435/288; 435/291; 435/810; 435/817; 436/94; 436/501; 204/403; 204/412
[58] Field of Search ............... 204/403, 153.12, 412; 435/288, 291, 810, 817, 6, 91; 436/501, 94

[56] References Cited
U.S. PATENT DOCUMENTS

| | | | |
|---|---|---|---|
| 4,882,013 | 11/1989 | Turner et al. | 204/403 |
| 5,008,182 | 4/1991 | Snimsky et al. | 435/6 |
| 5,079,351 | 1/1992 | Sninsky et al. | 435/810 |
| 5,185,243 | 2/1993 | Ullman et al. | 435/810 |

FOREIGN PATENT DOCUMENTS

| | | |
|---|---|---|
| 1223222 | 6/1987 | Canada . |
| 1223831 | 7/1987 | Canada . |
| 1231650 | 1/1988 | Canada . |
| 1236410 | 5/1988 | Canada . |
| 1249534 | 1/1989 | Canada . |
| 1293937 | 1/1992 | Canada . |
| 1297432 | 3/1992 | Canada . |

*Primary Examiner*—John Niebling
*Assistant Examiner*—Bruce F. Bell
*Attorney, Agent, or Firm*—Warren D. Woessner

[57] ABSTRACT

The present invention relates to a voltammetric sequence-selective sensor for target polynucleotide sequences which essentially comprises: an immobilized polynucleotide probe having one end covalently bound onto an amperometric electrode. The immobilized probe includes a target binding region capable of hybridizing to the target polynucleotide sequences forming an immobilized heteroduplex having at least a hybridized region. The sequence-selective sensor of the present invention also comprises means for voltammetrically detecting immobilized heteroduplexes. There is also provided a method for detecting the presence of a target polynucleotide analyte in a physiological sample, which comprises the steps of incubating the prepared physiological sample with the voltammetric sequence-selective sensor of the present invention; voltammetrically detecting immobilized heteroduplexes; and comparing the resulting voltammogram with a control voltammogram.

10 Claims, 2 Drawing Sheets

ACTIVATION OF GCE AND COUPLING OF DNA

ACTIVATION

COUPLING

ACTIVATION OF GCE AND COUPLING OF DNA

ACTIVATION

COUPLING

VOLTAMMETRIC SEQUENCE-SELECTIVE SENSOR FOR TARGET POLYNUCLEOTIDE SEQUENCES

BACKGROUND OF THE INVENTION

1. Field of the Invention

The present invention relates to a voltammetric sequence-selective sensor for target polynucleotide sequences, and more particularly to a polynucleotide probe having one end immobilized on an amperometric electrode and a target binding region.

2. Description of Prior Art

The application of recombinant DNA techniques is emerging as a powerful tool in the area of molecular diagnostic medicine. For example, the development of DNA and RNA molecular probes for the detection of viral and bacterial genomes and genetic defects in mammalian chromosomes may replace current immunochemical approaches.

Polynucleotide hybridization assays are used as research tools for the detection and identification of unique or specific polynucleotide sequences in samples of complete, fragmented, or mixed nucleic acids. Various hybridization diagnostic techniques have been developed.

The southern blot technique is based on a polynucleotide hybridization technique employing radiolabeled nucleic acid probes. This procedure permits autoradiographic detection of probe/analyte hybrids and identification of the polynucleotide sequence of the analyte. However, the Southern procedure, as well as the other diagnostic procedures employing radiolabeled nucleic acid probes, are very complex, time consuming, and have the additional problems and expenses generally associated with radioactive materials such as disposal and personnel monitoring. Thus, such assays have remained a tool of basic research and are not generally employed in applied or commercial areas such as clinical diagnosis.

Most of the existing methods used to attach a polynucleotide probe to a solid support are non-specific and the number of attachment sites per nucleic acid is difficult to control. It has been found that multiple attachment reduces the degree of freedom of the immobilized nucleic acid. The physical adsorption of single stranded DNA, covalent attachment via diazo-linkage, epoxidation, cyanogen bromide activation and photochemical reactions are associated with the complication of non-specific linkage between the nucleic acids and the solid support.

Canadian Patent 1,223,222, issued on Jun. 23, 1987, discloses an immobilized nucleic acid-containing probe coupled to a solid support in a manner which is site specific, which does not interfere with the ability of the nucleic acid to hybridize and which involves preferably a single chemical covalent linkage per nucleic acid to the solid support. Specifically, the nucleotide is coupled to the nucleic acid employing an enzyme and the nucleotide is chemically modified.

Canadian Patent 1,236,410, issued on May 10, 1988, discloses methods and reagents for determining the presence of specific DNA and RNA base sequences on single stranded target polynucleotides. The method involves the preparation of a specific single stranded ribonucleic acid or deoxyribonucleic acid molecule into which a bifunctional crosslinking molecule has been covalently incorporated. The incorporation is such that the crosslinking molecule retains the capacity to undergo a second addition to the nucleic acid of the bacterial, viral, or mammalian chromosome which is the target for the probe. The single stranded DNA or RNA probe is designed so that its nucleic acid base sequence is complementary to a unique region of the bacterial, viral, or mammalian chromosome target sequence. The nucleic acid, for example, from a blood, tissue, or cell sample is reacted with the probe under conditions where hybridization of the probe with the target will occur. Following hybridization, the sample is subjected to a photochemical or chemical procedure which causes crosslinking of the probe to the target complementary sequence. If no target genomic sequence is present, then no crosslinking of the probe will occur. In some cases hybridization of the probe to the target will precede both reactions of the bifunctional crosslinking reagent.

Canadian Patent 1,293,937 issued on Jan. 7, 1992, discloses polynucleotide probe compositions, diagnostic kits, and nonradiometric hybridization assays useful in the detection and identification of at least one target polynucleotide analyte in a physiological sample. There is provided a first polynucleotide probe having a catalyst attached thereto and which is substantially complementary to a first single-stranded region of the analyte; and a second polynucleotide probe having an apoluminescer attached thereto and which is substantially complementary to a second single-stranded region of the analyte. The second region is substantially mutually exclusive from the first region, such that upon hybridization of the first and second probes with the analyte, the catalyst and the apoluminescer are close enough to each other to permit the catalyst to act on a substrate to release a transformation radical to convert the apoluminescer to a luminescer.

U.S. Pat. No. 4,882,013 issued on Nov. 21, 1989, discloses the use of tetrathiafulvalene (TTF) and its derivatives as mediator molecules in the transfer of electrons between redox systems and electrodes in bioelectrochemical processes. There is also disclosed an assay procedure for assaying a substance based on this redox system and using an electrode. This assay does not include the detection of hybridized polynucleotide probes with a target polynucleotide since no redox system is involved in this hybridization.

Current methods for the diagnosis of inherited diseases employ digestion of a prepared DNA sample with restriction enzymes to form short, double-stranded segments, gel electrophoresis to separate these segments according to size, transfer of the separated segments to a thin membrane material, such as nylon, hybridization of the segments of interest with a labeled oligonucleotide (of complementary sequence to the known disease sequence), and detection of the label. The complete procedure requires about 24 hours, is labor-intensive, and is not readily automated. Furthermore, these methods usually employ radioactive labels, with their inherent safety and disposal problems. None of the above-mentioned diagnostic systems discloses a probe which can be treated to be reusable for hybridization. Thus, these systems are for a unique usage.

None of the above-mentioned diagnostic systems are highly sequence specific to enable the diagnosis of point mutation inherited diseases.

It would be highly desirable to be provided with a sequence-selective system for target polynucleotide sequences that uses a nonradiometric label in a system that is simple to use, highly specific and sensitive and reusable.

SUMMARY OF THE INVENTION

One aim of the present invention is to provide a sensor capable of precisely detecting target polynucleotide sequences which enables the diagnosis of inherited diseases such as sickle-cell anemia, β-thalassemia and cystic fibrosis.

Another aim of the present invention is to provide a system with a solid support having a polynucleotide probe immobilized thereon in a system that can be easily reset pursuant to an assay and may be continuously reused.

In accordance with the present invention, there is provided a voltammetric sequence-selective sensor for target polynucleotide sequences, which comprises:

a) an amperometric electrode;

b) an immobilized polynucleotide probe having one end covalently bound onto the electrode and the immobilized probe having a target binding region capable of hybridizing to the target polynucleotide sequences to form an immobilized heteroduplex having at least a hybridized region; and c) means for voltammetrically detecting the immobilized heteroduplex.

In accordance with the present invention, there is also provided a method for detecting the presence of a target polynucleotide analyte in a physiological sample, which comprises the steps of:

a) incubating the physiological sample with the voltammetric sequence-selective sensor in accordance with the present invention;

b) voltammetrically detecting the immobilized heteroduplex; and c) comparing the resulting voltammogram with a control voltammogram.

In accordance with the present invention, there is also provided a kit for detecting the presence of a target polynucleotide analyte in a physiological sample, which comprises:

a) an amperometric electrode;

b) an immobilized polynucleotide probe having one end covalently bound onto the electrode and the immobilized probe having a target binding region capable of hybridizing to the target polynucleotide sequences to form an immobilized heteroduplex having at least a hybridized region;

c) an electroactive complex which reversibly binds with heteroduplexes; and d) control polynucleotide sequences.

The voltammetric sequence-selective sensor in accordance with the present invention may be used for the detection of base pair mutation-associated diseases such as sickle-cell anemia, muscular dystrophy, osteodystrophy, phenylketonuria, hemophilia, hypercholesterolemia, thalassemia and cystic fibrosis.

DETAILED DESCRIPTION OF THE INVENTION

Figure 1:
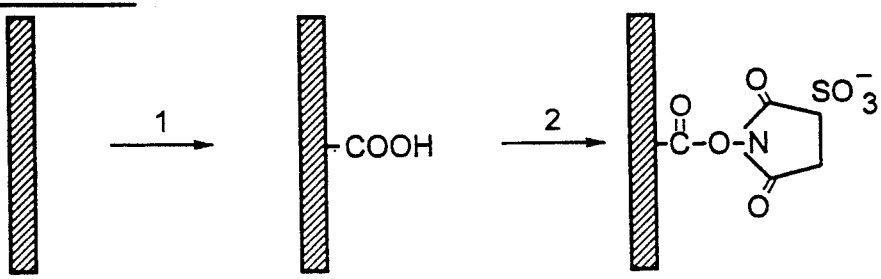
FIG. 1 is a scheme of the activation of glassy carbon electrodes and the covalent binding of the probe onto its surface.
Figure 1:
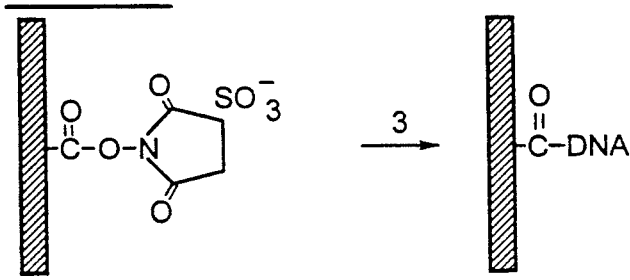

The sequence-selective DNA sensor is used to determine whether a particular DNA sequence is present in a sample containing DNA of unknown sequence. Applications of this sensor include the diagnosis of human or animal genetic disorders, such as cystic fibrosis or sickle-cell anemia, where the particular alterations in the normal DNA sequence that produce the disease are known. Among other applications, the sensor may also be used for the identification of certain viruses, for which components of the viral DNA sequence are known.

A sensor capable of detecting a precisely defined sequence of deoxyribonucleic acid (DNA) would have tremendous clinical utility in the diagnosis of inherited diseases such as sickle-cell anemia, β-thalassemia and cystic fibrosis. The DNA sensor of the present invention consists of single-stranded DNA (ssDNA) covalently bound to an electrode surface. Selective recognition of the complementary sequence results in double-strand formation. The double-stranded DNA (dsDNA) is then detected during or after exposure to a solution of a redox-active, DNA-binding complex that preconcentrates at the surface.

The sequence-selective sensor of the present invention is based on hybridization indicators and can replace existing procedures for the detection of known sequences of DNA in an unknown DNA sample.

Given an adequate quantity of analyte DNA (currently about 25 μg of complementary DNA), the sequence-selective sensor of the present invention can perform this determination in about 30 minutes. The sensor is reusable, and may be incorporated into an automated hybridization/rinse/measure/denature/rinse/measure instrument. The sensor of the present invention does not employ radioactive chemicals, and no special precautions are required for its use.

To prepare a physiological sample, DNA is isolated (e.g. from the white blood cells) and the region of interest is amplified using the polymerase chain reaction.

The voltammetric sequence-selective sensor of the present invention essentially comprises three components: 1) an amperometric electrode, 2) a sequence-selective polynucleotide probe and 3) a hybridization indicator.

1) Amperometric Electrode

The amperometric electrode is a device that monitors local changes in a physical property that occurs at the surface of the sensor, and converts this physical property into a measurable electronic signal. For the purposes of the sensor of the present invention, the amperometric electrode, measures the local concentration of a redox-active chemical species.

There may be used as an amperometric electrode in accordance with the present invention, glassy carbon electrode, graphite electrode, carbon fiber electrode, carbon paste electrode, reticulated vitreous carbon electrode, or metal electrodes onto which bifunctional reagents have been adsorbed, such as gold or platinum with adsorbed thiol- or disulfide-containing carboxylic acids.

2) Sequence-Selective Polynucleotide Probe

This is a chemical species having two components. The first consists of an oligodeoxynucleotide, approximately twenty base residues in length, that has a base sequence complementary to the base sequence in the target DNA. For example, the oligodeoxynucleotide sequence may be prepared to be complementary to a known human genetic disease sequence, or to a known viral DNA sequence. The second component is covalently bound to one end of this oligodeoxynucleotide, and consists of a chemically reactive group or series of reactive groups that allow covalent immobilization of the sequence recognition agent onto the electrode surface.

3) Hybridization Indicator

The hybridization indicator is employed after the electrode-sequence-selective probe sensor has been exposed to the target DNA. At this stage, sequence complementarity between the immobilized polynucleotide and the target DNA will result in hybridization, the formation of double-stranded DNA, at the electrode surface. The hybridization indicator is employed to indicate whether or not double-strand formation, and therefore sequence recognition, has occurred.

The hybridization indicator is a chemical species that interacts reversibly, in a measurably different way, with single-stranded DNA compared with double-stranded DNA. This interaction is measured by the electrode. An amperometric electrode requires a redox-active hybridization indicator.

There may be used as an hybridization indicator, tris(2,2'-bipyridyl)cobalt(III) perchlorate, or tris(1,10-phenanthroline)cobalt(III)perchlorate or any other electroactive compounds that bind to double-stranded DNA reversibly but not to single-stranded DNA, such as daunomycin or adriamycin or intercalating metalloporphyrins.

Direct Detection of the Local Hybridization Indicator Concentration at the Electrode Surface Tris(2,2'-bipyridyl)cobalt(III) perchlorate may be used as a hybridization indicator. It exhibits reversible redox activity and associates strongly with double-stranded DNA. Following exposure to target DNA, an electrode covalently modified with the sequence-selective polynucleotide probe is placed in a solution containing the cobalt complex. The complex binds to the double-stranded region of the DNA, so that its local concentration near the electrode surface is much higher than it is in the bulk of the solution. The local concentration of the cobalt complex is measured using standard voltammetric methods in a three-electrode cell, with the amperometric working electrode used in conjunction with standard reference and counter electrodes. The applied potential is scanned through the half-wave potential for the bound complex, and the magnitude of the peak current for the reduction of tris(2,2'-bipyridyl)cobalt(III) to tris(2,2'-bipyridyl)cobalt(II) is directly proportional to its local concentration at the electrode surface. If double-stranded DNA is not present on the electrode surface, this preconcentration of the cobalt complex does not occur, and the magnitude of the observed peak current is significantly lower.

Amplified Detection of the Local Hybridization Indicator Concentration

In addition to redox activity and reversible association with double-stranded DNA, the hybridization indicator employed may be capable of acting as a mediator in an enzymatic reaction. This is the case with tris(2,2'-bipyridyl)cobalt(II), since it can replace one of the two substrates, molecular oxygen, in the reaction catalyzed by the enzyme glucose oxidase (GOX):

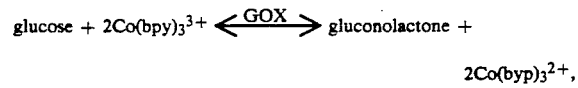

$$\text{glucose} + 2\text{Co(bpy)}_3^{3+} \xrightarrow{\text{GOX}} \text{gluconolactone} + 2\text{Co(bpy)}_3^{2+},$$

where (bpy) is 2,2'-bipyridyl. This enzymatic reaction can be employed to amplify the anodic response current obtained with the sensor. In addition to the complex itself, the detection solution now contains the enzyme GOX and its primary substrate, glucose, at a saturating concentration. The enzymatic reaction converts all $\text{Co(bpy)}_3^{3+}$ generated electrochemically at the sensor surface to $\text{Co(bpy)}_3^{2+}$; reoxidation of the +2 form to the +3 form of the complex completes the catalytic cycle, generating an amplified current response.

Diagnostic Applications

The sequence-selective DNA sensor of the present invention represents a new concept and a new class of sensing device. Applications in the prenatal diagnostics area are possible since the DNA sequence abnormalities associated with many inherited diseases are now known.

Examples include cystic fibrosis, muscular dystrophy, osteodystrophy, phenylketonuria, hemophilia, sickle-cell anemia, thalassemia and hypercholesterolemia.

With progress continually being made in the sequencing of the human genome, many more genetically-linked disorders will be diagnosable with the DNA sensor.

Several alterations in the normal human DNA sequence occur in individuals having cystic fibrosis. One of these sequence alterations involves a three-base deletion, called the delta $F_{504}$ deletion. Both the normal and disease DNA sequences are known at this site in the human genome. Synthetic oligonucleotides complementary to these sequences will be prepared, incorporated into a sequence recognition agent, and used in a DNA sensor to detect and diagnose cystic fibrosis from human DNA samples.

EXAMPLE I

Polynucleotide Probe Covalently Bound to an Amperometric Electrode

Activation of the Electrode Surface

Carboxylic acid groups were electrochemically generated on a polished (0.3 μm diamond paste) and rinsed glassy carbon electrode surface (GCE sold by Bioanalytical Systems, Inc., 0.075 cm² area) by oxidation at +1.5 V vs. Ag/AgCl for 15 seconds in aqueous 2.5% potassium dichromate with 10% nitric acid (1 of FIG. 1). The electrodes were then rinsed with deionized water and inverted. A 50 μL drop of a reagent solution containing 5 mM 1-(3-dimethylaminopropyl)-3-ethyl-carbodiimide (Aldrich) and 8 mM sodium N-hydroxysulfosuccinimide (supplied by Pierce*) in 0.020M potassium phosphate buffer, pH 6.9, was evaporated to dryness on the surface. Excess reagents were removed by rinsing with phosphate buffer, leaving N-hydroxysulfosuccinimide esters of the carboxylic acid groups on the electrode surface (2 of FIG. 1).

2) Preparation of the Sequence-Selective Polynucleotide Probe

Catalytic elongation of 225 μg oligo(dT)$_{20}$ (Sigma) in the presence of a 1000-fold molar excess of deoxyguanoxine triphosphate (dGTP, Boehringer) was accomplished with 250 units of terminal deoxynucletidyl transferase (E.C. 2.7.7.31, Boehringer) at 37° C. for 24 hours, according to the procedure outlined by Boehringer. Products were purified by phenol-chloroform extraction, reconstituted to 1 mg/mL in 0.020M phosphate buffer, pH 6.9, and characterized by polyacrylamide gel electrophoresis (BioRad).

3) Immobilization of the Sequence-Selective Polynucleotide Probe

Covalent immobilization occurred during the evaporation to dryness of 50 μL of a 1 mg/mL solution of the sequence-selective probe in 0.020M phosphate buffer, pH 6.9, from the activated GCE surface (3 of FIG. 1). Excess DNA was removed by extensive rinses with phosphate buffer. Electrodes thus modified were incubated for four hours prior to use in 5 mM tris(hydroxymethyl)aminomethane buffer, pH 7.1, with 20 mM sodium chloride and stored in this buffer at 4° C.

EXAMPLE II

Detection of Target Polynucleotide Sequence

1) Hybridization with Target DNA

GCEs modified with oligo(dT)$_{20}$(dG)$_{110}$ as described in Example I were exposed to a 1 mg/mL solution of analyte DNA, either oligo(dA)$_{20}$ (prepared in the Department of Biology, Concordia University, by standard phosphoramidite coupling chemistry) or poly(dA) (from denatured poly(dA)poly(dT), Boehringer), in 5 mM tris(hydroxymethyl)aminomethane buffer, pH 7.1, with 20 mM sodium chloride, for 15 minutes, to allow hybridization. The modified electrode was then rinsed with, and equilibrated in, the same buffer containing no DNA.

2) Detection Using the Hybridization Indicator

Prior to and following the hybridization step (1), the GCE covalently modified with the sequence recognition agent was placed in a water-jacketed (25° C.) three-electrode electrochemical cell containing a platinum wire auxiliary electrode, an Ag/AgCl reference electrode, and 10.00 mL of 5 mM Tris buffer, pH 7.1, with 20 mM NaCl. Cyclic voltammetry was performed using a Bioanalytical Systems 100A potentiostat, between +500 mV and −200 mV, at a scan rate of 0.050 V/s. Aliquots of a stock solution containing 5 mM tris(2,2'-bipyridyl)cobalt(III) in the same buffer were added, with cyclic voltammetry being performed after each addition, to construct calibration curves of peak current vs. concentration.

Figure 2:
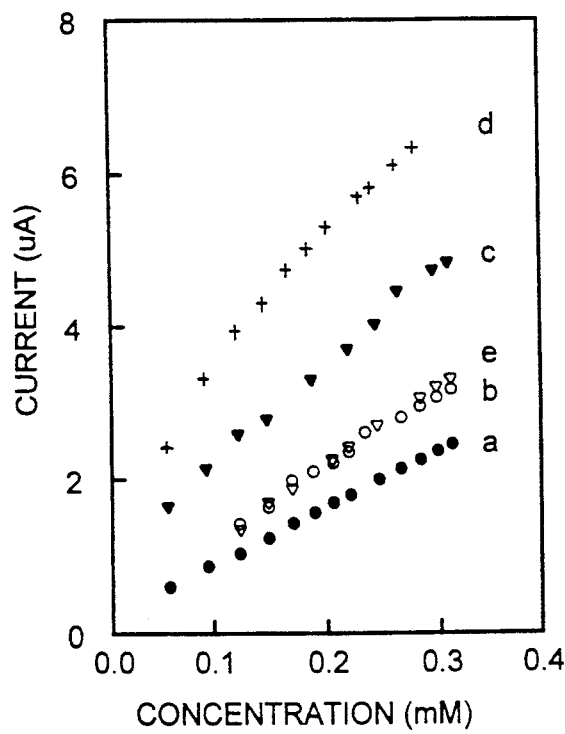
FIG. 2 is the calibration curves of voltammetric peak current for the reduction of $Co(bpy)_3^{3+}$ to $Co(bpy)_3^{2+}$ against $Co(bpy)_3^{3+}$ concentration.

Calibration curves of voltammetric peak current for the reduction of Co(bpy)$_3^{3+}$ to Co(bpy)$_3^{2+}$ against Co(bpy)$_3^{3+}$ concentration are given in FIG. 2. Five curves are shown, corresponding to (a) the signals observed at an unmodified GCE, (b) those seen at the GCE following modification with the sequence recognition agent, (c) peak currents observed after hybridization to oligo(dA)$_{20}$, (d) those seen after hybridization to a denatured solution of poly(dA)poly(dT), and (e) those seen after attempted hybridization to a model interferent, poly(dAdT).

The results given in FIG. 2 indicate (a) that the currents measured at the sensor depend on whether single- or double stranded DNA is present on the electrode surface, (b) that the hybridization indicator used, Co(bpy)$_3^{3+}$, interacts with both single- and double-stranded DNA, but that binding to double-stranded DNA occurs to a much greater extent, (c) that covalent immobilization does not interfere with the ability of the oligo(dT)$_{20}$ segment to recognize and hybridize with a complementary sequence, and (d) that a potential nonspecific interferent, such as poly(dAdT), will not give rise to increased signals, or "false positive" results.

Control immobilizations of the sequence recognition agent were performed in the absence of the carbodiimide and N-hydroxysulfosuccinimide coupling reagents to ensure that covalent immobilization, as opposed to adsorption, was occurring. These control electrodes yielded responses identical to those observed at the unmodified GCE.

Immobilizations were attempted with a variety of species of DNA in order to determine that deoxyguanosine residues were selectively bound to the activated GCE surface. Repeated attempts to immobilize denatured poly(dA)poly(dT) and native and denatured calf thymus DNA (42% GC content) were unsuccessful, while denatured poly(dG)poly(dC) yielded large response currents for Co(bpy)$_3^{3+}$.

Separate immobilizations were attempted with the synthetic oligodeoxynucleotides oligo(dG)$_{20}$ and oligo (dC)$_{20}$, followed by hybridizations with their complements; the results of these experiments indicated that increased current responses were only obtained for the oligo(dG)$_{20}$ immobilization. Taken together, these experiments show that consecutive deoxyguanosine residues are required for covalent immobilization using the carbodiimide/N-hydroxysulfosuccinimide reaction described above.

EXAMPLE III

Regeneration of the Sequence-Selective Sensor

Figure 3:
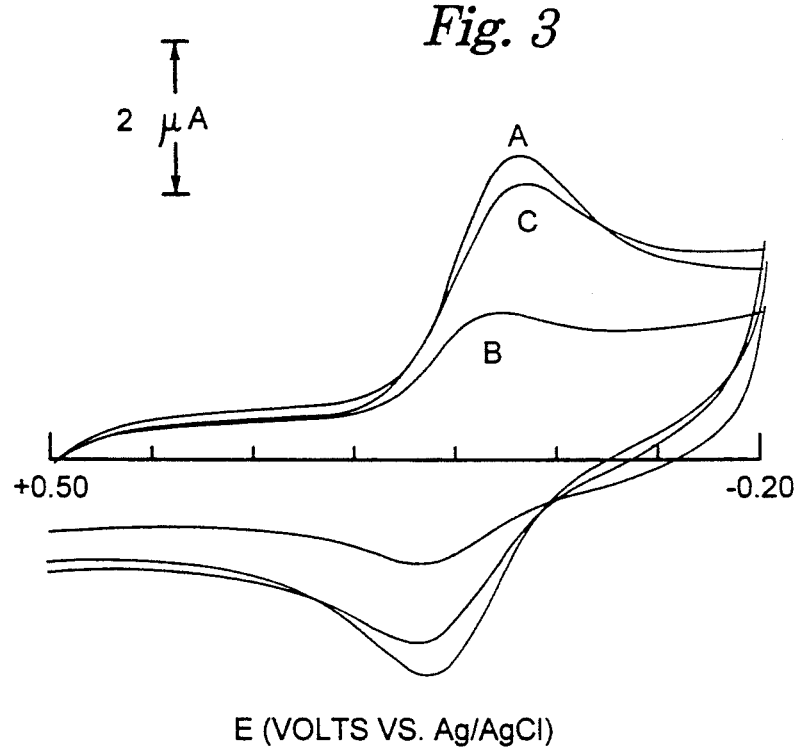
FIG. 3 is the cyclic voltammogram of repeated regeneration and hybridization with denatured poly(dA)-poly(dT).

Regeneration of single-stranded oligo(dT)$_{20}$ on the GCE surface was achieved by rinsing the modified electrode with hot, deionized water. Repeated regeneration and hybridization with denatured poly(dA)-poly(dT) yielded consistent signal decreases and increases, respectively. FIG. 3 shows cyclic voltammograms obtained over such a cycle of reuse. No significant signal deteriorations were observed over 10 regeneration/hybridization cycles, and average responses of 2.7±0.2 μA and 1.5±0.2 μA were obtained with 0.12 mM Co(bpy)$_3^{3+}$ after hybridization and regeneration, respectively. These results show that the DNA sensor of the present invention is reusable over multiple determinations.

FIG. 3 shows cyclic voltammograms of 0.12 mM Co(bpy)$_3^{3+}$ in 5 mM tris, pH 7.1, with 20 mM NaCl, at a GCE modified with oligo(dT)$_{20}$(dG)$_{110}$, after (A) hybridization to poly(dA), (B) denaturation by rinsing with hot, deionized water, and (C) rehybridization to poly(dA).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A voltammetric sequence-selective sensor for target polynucleotide sequences, comprising:
   a) an amperometric electrode;
   b) an immobilized polynucleotide probe having one end covalently bound onto said electrode and said immobilized probe having a target binding region is hybridized to said target polynucleotide sequences to form an immobilized heteroduplex having at least a hybridized region; and
   c) means for voltammetrically detecting said immobilized heteroduplex.

2. The voltammetric sequence-selective sensor according to claim 1, wherein said means for voltammetrically detecting comprises at least one electroactive complex which reversibly binds with heteroduplexes.

3. The voltammetric sequence-selective sensor according to claim 2, wherein said electroactive complex is a cobalt polypyridine complex.

4. The voltammetric sequence-selective sensor according to claim 1, wherein said covalently bound end of said probe comprises at least an oligo-d-G(100) sequence.

5. The voltammetric sequence-selective sensor according to claim 1, wherein said electrode is a carbon electrode.

6. The voltammetric sequence-selective sensor according to claim 1, wherein said sensor is reusable by rinsing in hot water.

7. A method for detecting the presence of a target polynucleotide analyte in a physiological sample, which comprises the steps of:
   a) incubating said physiological sample with the voltammetric sequence-selective sensor according to claim 1;
   b) voltammetrically detecting said immobilized heteroduplex; and
   c) comparing the resulting voltammogram with a control voltammogram.

8. A kit for detecting the presence of a target polynucleotide analyte in a physiological sample, comprising:
   a) an amperometric electrode;
   b) an immobilized polynucleotide probe having one end covalently bound onto said electrode and said immobilized probe having a target binding region capable of hybridizing to said target polynucleotide sequences to form an immobilized heteroduplex having at least a hybridized region;
   c) an electroactive complex which reversibly binds with heteroduplexes; and
   d) control polynucleotide sequences.

9. Method of using a voltammetric sequence-selective sensor according to claim 1 for the detection of base-pair mutation-associated diseases.

10. Method for using a voltammetric sequence selective sensor according to claim 2, wherein said base-pair mutation-associated diseases are selected from the group consisting of sickle-cell anemia, muscular dystrophy, osteodystrophy, phenylketonuria, hemophilia, hypercholesterolemia, thalassemia and cystic fibrosis.

* * * * *

(12) EX PARTE REEXAMINATION CERTIFICATE (7386th)
United States Patent
Mikkelsen et al.

(10) Number: US 5,312,527 C1
(45) Certificate Issued: Mar. 2, 2010

(54) VOLTAMMETRIC SEQUENCE-SELECTIVE SENSOR FOR TARGET POLYNUCLEOTIDE SEQUENCES

(75) Inventors: Susan R. Mikkelsen, Montreal (CA); Kelly M. Millan, LaSalle (CA); Aleksandrs J. Spurmanis, Montreal (CA)

(73) Assignee: Concordia University, Montreal, Quebec (CA)

Reexamination Request:
No. 90/009,183, Jun. 13, 2008

Reexamination Certificate for:
Patent No.: 5,312,527
Issued: May 17, 1994
Appl. No.: 07/957,602
Filed: Oct. 6, 1992

(51) Int. Cl.
*C12Q 1/68* (2006.01)
*G01N 33/543* (2006.01)

(52) U.S. Cl. .............................. 205/777.5; 204/403.01; 204/403.15; 204/412; 435/287.2; 435/810; 435/817; 436/94; 436/501

(58) Field of Classification Search .................. None
See application file for complete search history.

(56) References Cited

U.S. PATENT DOCUMENTS

| | | | |
|---|---|---|---|
| 4,452,889 A | 6/1984 | Sonoi et al. | |
| 4,749,647 A | 6/1988 | Thomas et al. | |
| 4,840,893 A | 6/1989 | Hill et al. | |
| 4,883,750 A | * 11/1989 | Whiteley et al. ............... | 435/6 |
| 4,945,045 A | 7/1990 | Forrest et al. | |
| 5,151,510 A | 9/1992 | Stec et al. | |
| 5,200,051 A | 4/1993 | Cozzette et al. | |
| 5,242,828 A | 9/1993 | Bergstrom et al. | |
| 5,510,481 A | 4/1996 | Bednarski et al. | |
| 5,776,672 A | 7/1998 | Hashimoto et al. | |

FOREIGN PATENT DOCUMENTS

| | | |
|---|---|---|
| CA | 1223222 | 6/1987 |
| EP | 0478319 A1 | 1/1992 |

OTHER PUBLICATIONS

Anthony P. F. Turner; Isao Karube, and George S. Wilson; Biosensors—Fundamentals and Applications; Oxford Science Publications; Oxford New York Tokyo, Oxford University Press, 1987; pp. 96; 157;267;269;309;312–313.

U.S. Appl. No. 07/766,064, filed Jul. 7, 1998, Hashimoto et al.

Gilmartin et al., "Comparative study of voltammetric behaviour of guanine at carbon and glassy electrodes . . . " The Analyst, 1613–1618, Oct. 1992.

* cited by examiner

*Primary Examiner*—Dwayne C Jones

(57) ABSTRACT

The present invention relates to a voltammetric sequence-selective sensor for target polynucleotide sequences which essentially comprises: an immobilized polynucleotide probe having one end covalently bound onto an amperometric electrode. The immobilized probe includes a target binding region capable of hybridizing to the target polynucleotide sequences forming an immobilized heteroduplex having at least a hybridized region. The sequence-selective sensor of the present invention also comprises means for voltammetrically detecting immobilized heteroduplexes. There is also provided a method for detecting the presence of a target polynucleotide analyte in a physiological sample, which comprises the steps of incubating the prepared physiological sample with the voltammetric sequence-selective sensor of the present invention; voltammetrically detecting immobilized heteroduplexes; and comparing the resulting voltammogram with a control voltammogram.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claim 4 is confirmed.

Claims 1–3 and 5–10 are cancelled.

* * * * *